(12) United States Patent
Björling et al.

(10) Patent No.: US 7,184,816 B2
(45) Date of Patent: Feb. 27, 2007

(54) CARDIAC STIMULATING AND DETECTING DEVICE, SYSTEM AND METHOD FOR IDENTIFYING FAR FIELD SIGNALS

(75) Inventors: Anders Björling, Järfälla (SE); Sven-Erik Hedberg, Kungsängen (SE); Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 199 days.

(21) Appl. No.: 10/864,064

(22) Filed: Jun. 9, 2004

(65) Prior Publication Data

US 2005/0004607 A1 Jan. 6, 2005

(30) Foreign Application Priority Data

Jun. 12, 2003 (SE) .................................. 0301743

(51) Int. Cl.
*A61B 5/04* (2006.01)
(52) U.S. Cl. .................. 600/509; 607/9; 607/14; 607/15; 600/515; 600/517; 128/901
(58) Field of Classification Search ............... 600/509, 600/515–517, 521; 607/9, 14, 15; 128/901
See application file for complete search history.

(56) References Cited

U.S. PATENT DOCUMENTS

| | | | |
|---|---|---|---|
| 5,275,621 A | 1/1994 | Mehra | |
| 5,720,768 A | 2/1998 | Verboven-Nelissen | |
| 5,978,708 A | 11/1999 | Bonnet et al. | |
| 6,070,100 A | 5/2000 | Bakels et al. | |
| 6,434,428 B1 | 8/2002 | Stoman et al. | |
| 6,477,416 B1 | 11/2002 | Florio et al. | |
| 6,526,311 B2 * | 2/2003 | Begemann | ............... 600/509 |
| 6,556,859 B1 * | 4/2003 | Wohlgemuth et al. | ...... 600/509 |
| 2002/0040191 A1 * | 4/2002 | Begemann | ............... 600/509 |
| 2002/0082650 A1 | 6/2002 | Stahrmann et al. | |
| 2002/0082653 A1 | 6/2002 | Stahmann et al. | |
| 2002/0128688 A1 | 9/2002 | Stoop et al. | |
| 2002/0183798 A1 | 12/2002 | Vonk | |

FOREIGN PATENT DOCUMENTS

WO WO 02/45797 6/2002

* cited by examiner

*Primary Examiner*—Robert Pezzuto
*Assistant Examiner*—Yun Haeng Lee
(74) *Attorney, Agent, or Firm*—Schiff Hardin LLP

(57) ABSTRACT

In an implantable heart stimulating device, system and method, a control circuit has first and second circuits for sensing and pacing. The first circuit can be connected to a first electrode member suited to be positioned in or at a first ventricle of the heart. The second circuit can be connected to a second electrode member suited to be positioned in or at a second ventricle of the heart. The control circuit is able to detect whether signals sensed by the second circuit are likely to be far field signals. The control circuit performs this detection by at least determining whether, during a predetermined time (length, more signals are sensed by the second circuit than by the first circuit.

35 Claims, 2 Drawing Sheets

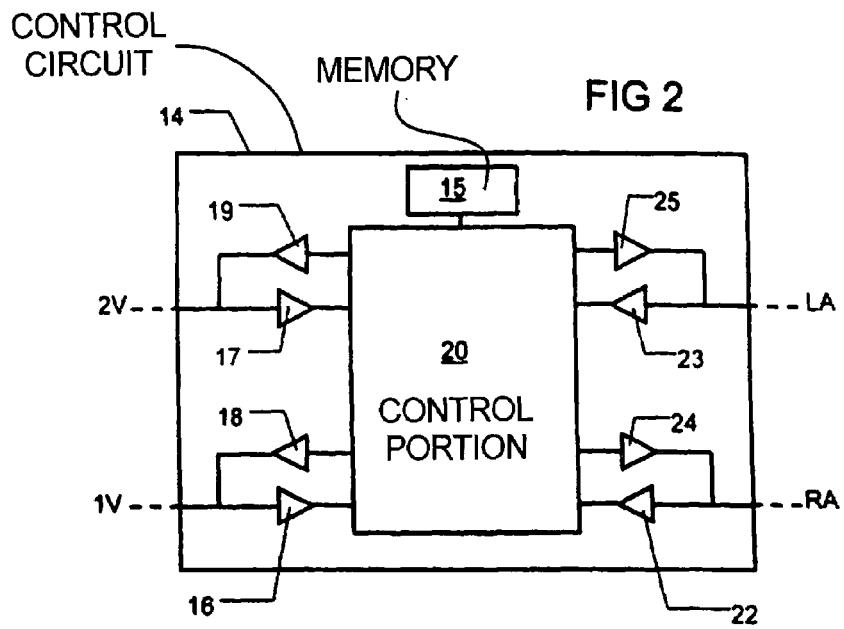
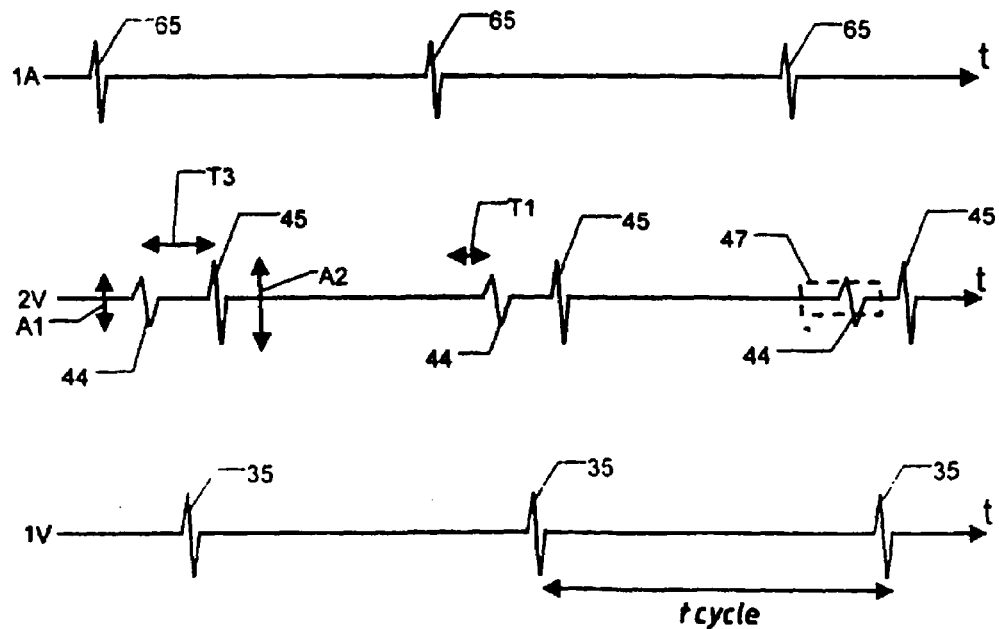

CARDIAC STIMULATING AND DETECTING DEVICE, SYSTEM AND METHOD FOR IDENTIFYING FAR FIELD SIGNALS

BACKGROUND OF THE INVENTION

1. Field of the Invention

The present invention relates to an implantable heart monitoring and stimulating device with which it is possible to stimulate both the ventricles of a heart, i.e. a bi-ventricular pacer. The invention also relates to a system including such a device and to a cardiac stimulating method.

2. Description of the Prior Art

Several different implantable devices for monitoring and stimulating a heart are known. The devices normally are able to sense the electrical activity of the heart and to deliver stimulation pulses to the heart. Some implantable devices are able to sense, and deliver stimulation pulses to, both the left and right ventricles of the heart.

Devices that are able to deliver stimulation pulses to both the left and right ventricle also are called bi-ventricular pacers. Such devices can be used to treat patients who suffer from different severe cardiac problems, e.g. patients suffering from congestive heart failure (CHF). CHF is defined generally as the inability of the heart to deliver a sufficient amount of blood to the body. CHF can have different causes. For example, it can be caused by a left bundle branch block (LBBB) or a right bundle branch block (RBBB). By using bi-ventricular pacing, the contraction of the ventricles can be controlled in order to improve the ability of the heart to pump blood. The stimulation pulses to the two ventricles can be delivered simultaneously but it is also known to deliver the stimulation pulses to the two ventricles with a short time delay between them in order to optimize the pumping performance of the heart.

U.S. Pat. No. 5,720,768 describes different possible electrode positions in order to stimulate or sense the different chambers of the heart.

U.S. Pat. No. 6,070,100 describes that electrodes may be positioned to sense and stimulate both the left atrium and the right atrium as well as the left and the right ventricles.

In connection with implantable heart stimulating devices, it is thus known to sense different signals with the help of the implanted electrodes and to control the heart stimulating device in response to the sensed signals. It is known, for example, to inhibit the delivery of a stimulating pulse if a natural, intrinsic, heart activity is detected. One difficulty in this context is to identify the signals that the device senses. Signals may originate from different intrinsic events in different parts of the heart. Signals may also originate from the heart stimulating device itself, i.e. from pulses delivered by different implanted electrodes. Signals even may have external causes, for example an external electromagnetic alternating field to which the person with the implanted device is exposed.

One kind of detected signal is a so-called far field signal. This is a signal that is detected by an implanted electrode, but which originates from some other part of the heart than that which it is intended to sense with the electrode in question. This phenomenon is known in connection with pacers arranged to sense or stimulate both the right atrium and the right ventricle. It is for example known that an electrode positioned in the right atrium may sense an R-wave, i.e. a QRS complex, when this electrode actually should sense a P-wave. The sensed R-wave is thus in this case a far field signal. Different ways to avoid this problem have been suggested in connection with pacers arranged to sense or pace the right atrium and the right ventricle.

In connection with bi-ventricular pacers, or four chamber pacers, different kinds of problems concerning far field detection may occur than those known in connection with pacers arranged to sense or pace only the right atrium and the right ventricle.

PCT Application WO 02/45797 describes systems and methods for distinguishing a valid sensed signal from an invalid signal, such as a myopotential. When sensing a left ventricular signal, the system starts an "intrinsic inhibition window". If and only if a right ventricular signal is sensed during this window, the sensed left ventricular signal is considered to be a valid sensed signal.

SUMMARY OF THE INVENTION

The present invention is based on the recognition that a particular problem that may occur in a bi-ventricular heart stimulating device is that far field atrial signals can be sensed by a ventricular sense electrode. In a bi-ventricular heart stimulating device, the electrode for sensing events of the left ventricle is often introduced via the coronary sinus into a cardiac vein. The position of this electrode is particularly vulnerable to sense far field signals, in particular a far field P-wave from the left atrium. The problem may occur both in a device with one or two atrial electrodes and in a device without any atrial electrode. When an atrial electrode is present, then the far field signal can originate either in a paced atrial event or a non-paced atrial event. When no atrial electrode is present, the far field signal, if it is an atrial event, can evidently only be a non-paced event, i.e. an intrinsic atrial event. A sensed far field signal may cause the device to operate inappropriately, since this event may be interpreted by the device as, for example, an intrinsic left ventricular event.

An object of the present invention therefore is to provide an implantable heart stimulating device with which it is possible to detect whether one or more signals sensed by a ventricular electrode are likely to be far field signals from an atrium. A more particular object is to detect whether one or more signals sensed by means arranged to be able to sense the left ventricle are likely to be far field atrial signals, in particular of the kind that may originate from the left atrium.

The above object is achieved by an implantable heart stimulating device having a control circuit with a first circuit for sensing and pacing adapted to be connected to at least a first electrode member suited to be positioned in or at a first ventricle of the heart so as to transfer signals to and receive signals from the first circuit such that the first circuit is able to sense and pace the first ventricle, and a second circuit for sensing and pacing adapted to be connected to at least a second electrode member suited to be positioned in or at a second ventricle of the heart so as to transfer signals to and receive signals from the second circuit such that the second circuit is able to sense and pace the second ventricle.

The control circuit also detects whether one or more signals sensed by the second circuit are likely to be far field signals, the control circuit performing this detection by at least determining whether, during a predetermined time length, more signals are sensed by the second circuitry than by the first circuit.

As used herein "sensing" a signal means that the control circuit detects a signal of a kind that is typical for a cardiac event. In particular, the control circuit may be arranged to detect a signal that is typical for a QRS-complex, i.e. for a ventricular depolarisation. When the device is in use in a living being, the "sensed signal" is thus a cardiac event sensed by the control circuit. How to arrange the control circuit in order to sense cardiac events are known to those skilled in the art.

Normally, the number of events sensed by the first circuit should be the same as the number of events sensed by the second circuit. In other words: the number of R-waves (QRS-complex) sensed by the first circuit ought to be the same as the number of R-waves sensed by the second circuit. If more events are sensed by the second circuit than by the first circuit, this is a strong indication of the fact that at least some of the events sensed by the second circuit are far field signals. Since the control circuit determines whether more signals are sensed by the second circuit than by the first circuit, the control circuit is thus able to detect whether some signals sensed by the second circuit are likely to be far field signals.

The aforementioned predetermined time length corresponds to one or more time cycles of a length corresponding to a normal heart cycle. Preferably, the predetermined time length covers at least two of such time cycles. By detecting the number of signals during a sufficiently long time, the reliability of the detection is increased. It should be noted that when the detection is carried out over a number of time cycles, these time cycles could either be consecutive time cycles or non-consecutive time cycles.

In an embodiment of the device according to the invention, the control circuit operates such that no pacing pulses are delivered by the first and second circuits during the time when the detection is carried out. By this measure the detection becomes more accurate.

The control circuit can perform the detection by at least determining whether, during the predetermined time length (the number of signals sensed by said second circuit)>x·(the number of signals sensed by said first circuit), where x is a preset number $\geqq 1$. For example, x may be a suitable preprogrammed number.

In a further embodiment, the control circuit performs the detection by at least determining whether, during the predetermined time length, the number of signals sensed by said second circuit is substantially twice the number of signals sensed by said first circuit. By "substantially twice" is meant either exactly twice or within a predefined interval around 2. For example, between 1.9 and 2.1 times the number of signals sensed by the first circuit. If the number of signals sensed by the second circuit is substantially twice the number of signals sensed by the first circuit, this is a further indication of the fact that the second circuit senses far field signals. This is an indication of the fact that during each heart cycle, the second circuit senses both an atrial event and a ventricular event.

According to a further embodiment of the invention, the control circuit determines the amplitudes of at least the signals sensed by the second circuit at least during the time when the detection is carried out, and the control circuit also takes into account the difference in amplitude when determining whether a signal is likely to be a far field signal. Since normally a far field signal is weaker than the ventricular event that it is intended to sense, the amplitudes of the far field signals will probably be lower. By considering the amplitudes of the sensed signals, a further indication of the fact that some signals are far field signals is obtained. By considering the amplitudes it is also possible to determine which of the signals that are likely to be far field signals.

According to another embodiment of the invention, the control circuit determines whether the amplitudes of the signals sensed by the second circuit at least during the time when the detection is carried out fall into two categories: a first category of signals with an amplitude within a first, higher amplitude range and a second category of signals with an amplitude within a second, lower amplitude range, and the control circuit takes into account the fact that the signals fall into two such amplitude-categories when determining whether a signal is likely to be a far field signal. By categorizing the signals in this manner, it can be assumed to be likely that the signals within the lower amplitude range are far field signals.

According to another embodiment of the invention, the control circuit determines whether the shape of the signals sensed by the second circuit, at least during the time when the detection is carried out, falls into two categories: a first category of signals with a first type of shape and a second category of signals with a second type of shape, and the control circuit takes into account the fact that the signals fall into two such shape-categories when determining whether a signal is likely to be a far field signal. The far field signals can have a different shape than the signals that it is intended to detect. By taking the shape of the signals into account, a further indication of whether far field signals are present is obtained.

According to another embodiment of the invention, the control circuit, at least during the time when the detection is carried out, determines the distance in time between consecutive signals sensed by the second circuit, and the control circuit takes this determined distance in time into account when determining whether a signal is likely to be a far field signal. Preferably, the control circuit determines whether the distance in time between the consecutive signals is less than a predetermined time $t_{LL}$. The predetermined time $t_{LL}$ is, for example, less than 500 ms. If different signals detected by the second circuit occur near each other in time, this is a further indication that far field signals are likely to be present.

The control circuit can determine whether such consecutive signals, between which the distance in time is less than $t_{LL}$, occur a predetermined number of times or with a predetermined frequency, during one or more periods of time during which the detection is carried out, and the control circuit takes into account that the consecutive signals occur at least a predetermined number of times, or with at least a predetermined frequency, when determining whether a signal is likely to be a far field signal. If repeatedly consecutive signals occur with a short time between them, this makes it even more likely that far field signals are present.

According to another embodiment of the invention, the control circuit also includes a third circuit for sensing and/or pacing adapted to be connected to at least a third electrode member suited to be positioned in or at a first atrium of the heart so as to transfer signals to and/or receive signals from the third circuit such that the third circuit is able to sense and/or pace said first atrium. The first atrium can be either the right atrium or the left atrium, preferably the right atrium.

The control circuit also can determine a first time interval T1 between a paced or sensed event of the third circuit and a subsequent sensed event of the second circuit, and determine whether T1<TA, where TA is a preset time, and the control circuit takes into account the fact that one or more such situations where T1<TA occur when determining whether a signal is likely to be a far field signal. Suitably 50 ms$\leqq$TA$\leqq$150 ms. If a signal is sensed by the second circuit at a very short point in time after a paced or sensed event by the third circuit, this is a further indication of the fact that the signal sensed by the second circuit is likely to be a far field signal.

Preferably, the control circuit carries out at least one measure (reaction) when at least a predetermined number of the signals which are likely to be far field signals have been detected. The device thus carries out a suitable measure when far field signals have been detected.

According to a preferred embodiment, the device has at least one memory, and said measure is that an indication of the fact that suspected far field signals have been detected is stored in said memory. Since the detection of far field signals has been stored in the memory, it is possible for a physician to analyze the occurrence of detected far field signals at a medical check-up.

The measure also can be that a sensing threshold of the second circuit is increased. By increasing a sensing threshold, it is less likely that the second circuit will detect far field signals.

Another possible measure is that the operation of the device is set such that possible events sensed by the second circuit does not influence the operation of the device. If events detected by the second circuit do not influence the operation of the device, possible far field signals detected by the second means cannot lead to an inappropriate operation of the device.

The control circuit also can take into account the shape of the signals sensed by the second circuit. The measure then can also be that the operation of the device is set such that possible signals which are sensed by the second circuit and which have a shape typical for the detected suspected far field signals do not influence the operation of the device. Also in this manner it is possible to avoid that detected far field signals influence the operation of the device.

The control circuit also can operate according to a time cycle corresponding to a normal heart cycle. The measure can be that the operation of the control circuit is changed to set a blanking period which covers at least the part of the time cycle which corresponds to the occurrence in the time cycle of the signals, sensed by the second circuit, which have been determined to be likely to be far field signals, and the operation of the device is set such that possible signals sensed by the second circuit during the blanking periods do not influence the operation of the device. By the use of such blanking periods it is also possible to avoid the far field signals from having an influence on the operation of the device.

It should be noted that the aforementioned time cycle can be determined by simply defining a normal time for a heart cycle, for example about 1s, or by detecting events which signify a heart cycle.

The invention also concerns an implantable heart stimulating system having an implantable heart stimulating device according to any of the preceding embodiments, and at least a first electrode member and a second electrode member connected to the device. Preferably, this system also has at least a first lead and a second lead connected to the device, the said first electrode member being arranged on the first lead and the second electrode member being arranged on the second lead. With such a system, the above-mentioned advantages are obtained.

The invention also concerns a cardiac stimulation method wherein the system is implanted in a human or animal being and the first electrode member is positioned in or at a first of the ventricles of the heart of the human or animal being and the second electrode member is positioned in or at the second ventricle of the heart. Preferably, the first ventricle is the right ventricle and the second ventricle is the left ventricle of the heart. With this method, the above-mentioned advantages of the invention are achieved.

According to another embodiment of the method, the control circuit also has a third circuit for sensing and/or pacing an atrium, and the system has a third lead with a third electrode member, and the third lead is connected to the third circuit, and the third electrode member is positioned in or at a first atrium of the heart such that said third circuit is able to sense and/or pace the first atrium. Preferably, the first atrium is the right atrium of said heart.

The system preferably is used on a human or animal being suffering from congestive heart failure. In particular on a human or animal being suffering from a left or right bundle branch block. For example, on a human or animal being in which the AV-node has been ablated.

Preferably, the system is used to avoid the operation of the device from being affected by far field P-waves sensed by the second circuit.

The device preferably has at least one memory and is used such that information about the detection of one or more suspected far field signals sensed by the second circuit is stored in the memory allowing this information to be accessible to a physician at a medical check-up.

BRIEF DESCRIPTION OF THE DRAWINGS

FIG. 2 shows schematically a control circuit in accordance with the invention which forms part of the device of FIG. 1.

FIG. 3 shows schematically on a time scale signals sensed by first, second and third circuits in accordance with the invention.

DESCRIPTION OF THE PREFERRED EMBODIMENTS

Figure 1:
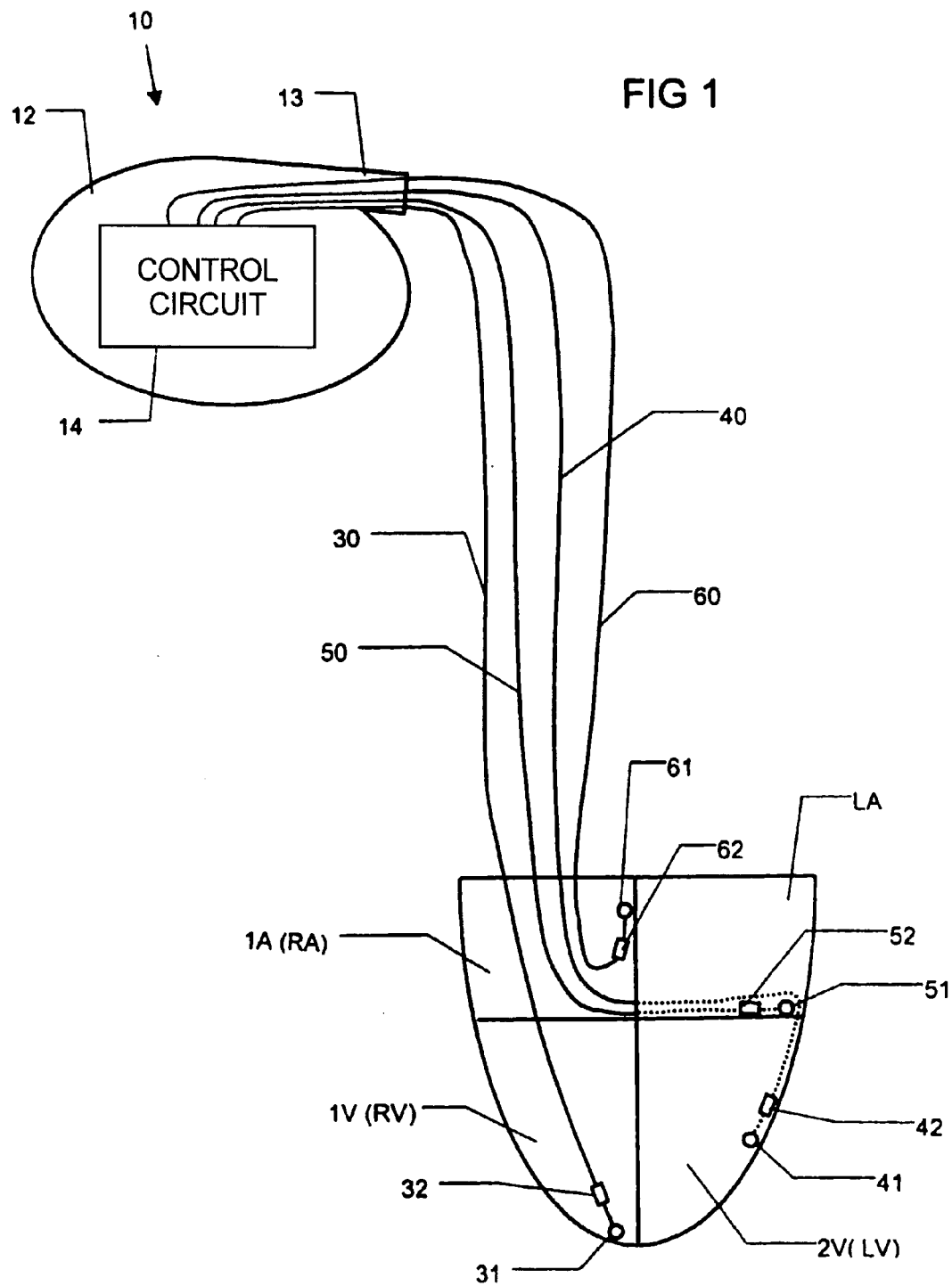
FIG. 1 shows schematically a heart stimulating system with a heart stimulating device connected to leads with electrode members positioned in a heart.

FIG. 1 shows schematically an implantable heart stimulating device 10 according to the invention. The device 10 has a housing 12. The device 10 includes a control circuit 14 (that will be described more in connection with FIG. 2). The device 10 has a connector portion 13. The device 10 is in the illustrated embodiment connected to different leads 30, 40, 50, 60.

FIG. 1 also schematically shows a heart including a right atrium RA, a left atrium LA, a right ventricle RV and a left ventricle LV.

A first lead 30 has a first electrode member 31, 32 positioned in a first ventricle 1V (the right ventricle RV) of the heart. The electrode 31 may be called tip electrode and the electrode 32 can be called a ring electrode. In this example, the first lead 30 thus includes bipolar electrodes. However, it is within the scope of the invention that instead the device 10 is connected to unipolar electrodes as is known to those skilled in the art. The first electrode member 31, 32 can be used to sense cardiac events related to said first ventricle 1V (in this case the right ventricle RV). The first electrode member 31, 32 can also be used for delivering stimulation signals to the first ventricle 1V.

A second lead 40 is connected to the device 10. The second lead 40 includes in the shown embodiment bipolar electrodes 41, 42. These electrodes constitute a second electrode member 41, 42 positioned for sensing events related to the second ventricle 2V (the left ventricle LV). The electrode member 41, 42 is also used to deliver stimulation signals to the second ventricle 2V. The second lead 40 may for example be introduced via the right atrium and the coronary sinus such that the electrode member 41, 42 is positioned in for example the middle or great cardiac vein of the heart. How to introduce the second lead 40 in this manner is known to a person skilled in the art.

According to the shown embodiment, the device is also connected to a third lead 60 with a third electrode member 61, 62. This electrode member is positioned in a first atrium 1A (the right atrium RA) in order to be able to sense and stimulate this atrium. The device 10 is in this case also connected to a fourth lead 50 with an electrode member 51, 52. This electrode member may be positioned in the coronary sinus in order to sense and stimulate the left atrium LA of the heart.

The device 10 together with at least two leads 30, 40 thus constitute an implantable heart stimulating system according to the invention.

FIG. 2 shows schematically the control circuit 14 in some more detail. The control circuit 14 includes at least one memory 15. Furthermore, the control circuit 14 has a first circuit 16, 18 adapted to be connected to the first lead 30 in order to sense and stimulate the first ventricle 1V. The circuit 16, 18 is also connected to a control portion 20 of the control circuit 14.

The control circuit 14 also includes a second circuit 17, 19 adapted to be connected to the second lead 40 in order to sense and stimulate the second ventricle 2V. The circuit 17, 19 is also connected to the control portion 20 of the control circuit 14.

The control circuit 14 illustrated in FIG. 2 also has a third circuit 22, 24 adapted to be connected to the third lead 60 in order to sense and stimulate the right atrium RA. The control circuit 14 also includes a fourth circuit 23, 25 adapted to be connected to the fourth lead 50 in order to sense and stimulate the left atrium LA.

Each of the first, second, third and fourth circuits for sensing and pacing includes the necessary components for fulfilling this function. For example the first circuit 16, 18 may include a sense amplifier 16 and a pacing circuit 18. The control circuit 14 is arranged such that the different circuits in particular are able to sense P-waves and R-waves. The control circuit 14 may of course also be arranged to be able to sense for example evoked responses to delivered pacing pulses. However, in connection with the present invention, it is the detection of P-waves and R-waves that is most important.

Since a control circuit 14 for controlling a pacer is well known to a person skilled in the art, no further details need to be described here. FIG. 2 only functionally shows some of the parts of the control circuit 14 and the control circuit 14 does not necessarily have to be designed in the manner indicated in FIG. 2. The control circuit 14 may of course include several other parts. For example the control circuit 14 can be arranged to control the heart stimulating device 10 by sensing the activity of the living being into which the device 10 is implanted. Furthermore, the control circuit 14 can be arranged such that it can communicate via so-called telemetry with an external device. The control circuit 14 may also for example include means for delivering defibrillation signals. It may also be noted that the control circuit 14 may include several different memories, such as a RAM and a ROM. The memory 15 shown may thus be any suitable memory included in the control circuit 14.

The control circuit 14 is arranged to be able to detect or determine and to operate according to time cycles corresponding to a normal heart cycles. This can be done by detecting events in the heart corresponding to a heart cycle. It is also possible to determine a heart cycle by simply setting a time (for example about 1s) that corresponds to a normal heart cycle. The time can for example be set in response to a paced or sensed event and can thereby constitute an escape interval.

FIG. 3 illustrates schematically signals sensed by different means on a time scale t. The upper line in FIG. 3 relates to events, i.e. signals 65, sensed by the third circuit 22, 24. These signals 65 are thus sensed via the third electrode member 61, 62 which are positioned to sense events in the first atrium 1A, in this case the right atrium RA.

The second line in FIG. 3 indicates in a corresponding manner signals 44, 45 sensed by the second circuit 17, 19. These signals 44, 45 are thus sensed via the second electrode member 41, 42 that is positioned to sense events in the second ventricle 2V, in this case the left ventricle LV.

The bottom line in FIG. 3 indicates in a corresponding manner signals 35 sensed by the first circuit 16, 18. These signals 35 are thus sensed via the first electrode member 31, 32 that is positioned to sense events in the first ventricle 1V, i.e. in this case the right ventricle RV.

As has been explained above, it is possible that the second circuit 17, 19 not only senses events of the second ventricle 2V but also senses far field signals. In particular, there is a risk that the second circuit 17, 19, which is connected to the second electrode member 41, 42, senses far field signals that in fact relate to atrial events. In FIG. 3 it can be assumed that the signals 44 are such far field signals, while the signals 45 are real events of the left ventricle 2V.

According to the present invention, the control circuit 14 is wired or programmed to be able to detect whether one or more signals sensed by the second circuit 17, 19 is likely to be far field signals. The control circuit 14 performs this detection by at least determining whether during a predetermined time length, more signals are sensed by the second circuit 17, 19 than by the first circuit 16, 18. The predetermined time length may cover one or more time cycles of a length that corresponds to a normal heart cycle. One such time cycle $t_{cycle}$ is indicated in FIG. 3. FIG. 3 thus illustrates about two such time cycles $t_{cycle}$. The detection can be carried out over consecutive time cycles $t_{cycle}$ but it is also possible to arrange the control circuit 14 such that the detection of possible far field signals is done intermittently at predetermined intervals. When this detection is carried out, the control circuit 14 is preferably arranged such that no pacing pulses are delivered by the first 16, 18 and second 17, 19 circuits during the time when the detection is carried out. Such possible delivered pulses may otherwise make it more difficult to analyse whether far field signals are present.

The control circuit 14 can be arranged to perform the detection by determining whether (the number of signals 44, 45 sensed by the second circuit 17, 19) is larger than x times (the number of signals 35 sensed by the first circuit 16, 18), where x is a preset number $\geq 1$. x is thus preferably a preprogrammed number. x can for example be 1.2. The control circuit 14 can also be arranged to detect whether the number of signals sensed by the second circuit 17, 19 is substantially twice the number of signals sensed by the first circuit 16, 18. As can be seen in FIG. 3, the number of signals 44, 45 sensed by the second circuit 17, 19 is exactly twice the number of signals 35 sensed by the first circuit 16, 18. This is a strong indication of the fact that the second circuit 17, 19 also senses far field signals 44 in addition to the ventricular signals 45.

In addition to the above manner of determining whether the second circuit 17, 19 is likely to detect far field signals, the control circuit 14 can perform other detections in order to increase the reliability of the detection of far field signals and in order to be able to determine which signals of the signals 44, 45 detected by the second circuit 17, 19 that are likely to be far field signals. Different further manners in which the control circuit 14 can be arranged to perform this detection will be described below under the headings I to IV. It is to be understood that the control circuit 14 can be arranged to perform all these detections I to IV. It is however also within the scope of the invention that the control circuit 14 is arranged to only include one, two or three of these manners I to IV.

I

The control circuit 14 determines the amplitudes of the signals 44, 45 sensed by the second circuit 17, 19. The control circuit 14 is thus arranged to take the difference in amplitude into account when determining whether signals are likely to be far field signals. As can be seen in FIG. 3, the signals 44 have a lower amplitude A1 than the signals 45, which have an amplitude A2 (the amplitudes are in FIG. 3 indicated as peak-to-peak values). The signals 44 with the lower amplitude A1 are likely to be far field signals. The control circuit 14 can thus be arranged to determine whether the amplitudes A1, A2 of the signals 44, 45 sensed by the second circuit 17, 19 fall into two categories: a first category of signals with an amplitude A2 within a first higher amplitude range and a second category of signals with an amplitude A1 within a second lower amplitude range. The control circuit 14 can be arranged to automatically categorise the signals 44, 45 in such categories by detecting whether signals 44 within a lower amplitude range are detected while other signals 45 fall within a higher amplitude range.

II

The control circuit 14 can also be arranged to detect the shape of the detected signals 44, 45. Such a morphology-detector may for example work by integrating the signal and additionally consider the amplitude of the signal as well as possibly the derivatives of the signal, which indicate how steep the signal is. The control circuit 14 can thus be arranged to determine whether the shape of the signals falls into two categories: the first category of signals with a first type of shape and a second category of signals with the second type of shape. The far field signals 44, which are far field P-waves, are likely to have a different shape than the signals 45 that are ventricular R-waves. The shape of the signals may thus be taken into account when determining which signals that are far field signals.

III

The control circuit 14 is arranged to determine the distance in time T3 between consecutive signals sensed by the second circuit 17, 19. The control circuit 14 is thereby arranged to take this determined distance in time T3 into account when determining whether a signal is likely to be a far field signal. In particular, the control circuit 14 can be arranged to determine whether the time T3 is less than a predetermined time $t_{LL}$. $t_{LL}$ is normally less than 500 ms, for example less than 300 ms. When signals 44, 45 occur close to each other in time, it is likely that some signals 44 are far field signals.

The control circuit 14 can be arranged to determine whether such consecutive signals 44, 45, between which the time is less than $t_{LL}$, occur a predetermined number of times or with a predetermined frequency during the time period during which the detection is carried out. If such signals 44, 45 repeatedly occur in pairs within the time $t_{LL}$, then it is likely that far field signals 44 are detected by the second circuit 17, 19. The control circuit 14 can thus be arranged to indicate that far field signals 44 are present in case repeatedly such pairs of signals 44, 45 are detected.

IV

In case the device is also provided with a third circuit 22, 24 for sensing and/or pacing an atrium, then it is also possible to consider paced and/or sensed event by the circuit means 22, 24 when determining whether the second circuit 17, 19 are sensing far field signals. In particular, the control circuit 14 can determine a time interval T1 between a paced or sensed event 65 of the third circuit 22, 24 and a subsequent sensed event 44 of the second circuit 17, 19. The control circuit 14 can determine whether T1<TA, where TA is a preset time. The control circuit 14 can thus be arranged to also take this fact into account when determining whether a signal 44 is likely to be a far field signal. Preferably, 50 ms≦TA≦150 ms.

When the control circuit 14 has determined that some signals 44 that are detected by the second circuit 17, 19 are far field signals, the control circuit 14 is preferably arranged to carry out one or more measures in response to this detection. One such measure can be that an indication is stored in the memory 15 of the fact that suspected far field signals 44 have been detected. Also the moments in time when such far field signals were detected can be stored in the memory 15. Another measure is that the control circuit 14 can be arranged to increase a sensing threshold of the second circuit 17, 19. By increasing the sensing threshold for detecting R-waves, it is less likely that the control circuit 14 will detect the far field signals 44, since these signals 44 normally have a lower amplitude than the signals 45.

Another possible measure is that the operation of the device 10 is set such that signals or events sensed by the second circuit 17, 19 do not influence the operation of the device 10. Neither the signals 44 nor the signals 45 are thus used to control for example certain escape intervals. Instead, according to this possible embodiment, the operation of the device 10 is controlled by other means, for example by signals 65 sensed by the third circuit 22, 24 and/or by signals 35 sensed by the first circuit 16, 18. This embodiment is particularly advantageous in case it is not possible to distinguish the far field signals 44 from the detected R-waves 45.

If the control circuit 14 has a morphology detector in accordance with point 11 above, the measure can be that the operation of the device 10 is set such that possible signals which are sensed by the second circuit 17, 19 and which have a shape typical for the detected far field signals 44 do not influence the operation of the device 10. According to this embodiment, the signals 44 are thus distinguished from the signals 45 by their shape. The control circuit 14 can thus be arranged such that the operation of the device 10 is influenced by the signals 45 but not by the signals 44.

If the signals 44 have been distinguished from the signals 45, for example in any of the above described manners, it is also possible that the control circuit 14 is arranged to operate with blanking periods which cover the part of the time cycle which corresponds to the occurrence of the signals 44. In FIG. 3, one such blanking period 47 has been marked. In order to make the illustration in FIG. 3 clear, this blanking period 47 has only been marked in one time cycle, but of course the blanking period 47 should occur in every time cycle corresponding to a normal heart cycle. This measure is particularly useful if it has been shown that the far field signals 44 repeatedly occur within the same portion of the heart cycle. The control circuit 14 is thus arranged such that the operation of the device does not depend on signals detected by the second means 17, 19 during the blanking periods 47.

The invention also relates to a system and to the use of a system. The system comprises an implantable heart stimulating device 10 according to the above together with at least a first electrode member 31, 32 and a second electrode member 41, 42 connected to the device 10. These electrode members 31, 32, 41, 42 are connected via the first lead 30 and the second lead 40. This system is used such that it is implanted in a human or animal being. The first electrode member 31, 32 is positioned in or at a first ventricle 1V of the heart. The second electrode member 41, 42 is positioned in or at the second ventricle 2V of the heart. The second ventricle 2V is here the left ventricle. The system may also be used with third circuit 22, 24 for sensing and/or pacing an atrium. A third lead 60 with a third electrode member 61, 62 may be positioned in the heart and connected to the third circuit 22, 24 such that the third circuit 22, 24 are able to sense and/or pace the first atrium 1A of the heart. The first atrium 1A is in this case for example the right atrium RA.

The system may be used on a human or animal being suffering from congestive heart failure, for example caused by a left or right bundle branch block. The system may also be used on a human or animal being in which the AV-node has been ablated. The system is used in order to avoid that the operation of the device 10 is affected by far field P-waves sensed by the second circuit 17, 19. Preferably, the system is used such that information about the detection of suspected far field signals are stored in the memory 15 such that this information is accessible to a physician at the medical checkup.

Although modifications and changes may be suggested by those skilled in the art, it is the intention of the inventors to embody within the patent warranted hereon all changes and modifications as reasonably and properly come within the scope of their contribution to the art.

We claim as our invention:

1. An implantable heart stimulating device comprising:
    a first sensing and pacing circuit adapted for interaction with a first ventricle of a heart for delivering pacing pulses to and for receiving signals from the first ventricle;
    a second sensing and pacing circuit adapted for interaction with a second ventricle of the heart for delivering pacing pulses to and for receiving signals from the second ventricle; and
    a control circuit connected to said first and second sensing and pacing circuits for detecting whether a signal received by said second sensing and pacing circuit is likely to be a far field signal, by determining whether, during a predetermined time duration corresponding to at least one normal heart cycle of the patient, more signals are received by said second circuit than by said first circuit.

2. An implantable heart stimulating device as claimed in claim 1 wherein said control circuit performs said detection during a detection time in said predetermined time duration, and wherein said control circuit controls each of said first and second sensing and pacing circuits for causing no pacing pulses to be delivered during said detection time.

3. An implantable heart stimulating device as claimed in claim 1 wherein said control circuit, during said predetermined time duration, determines whether a number of signals detected by said second circuit exceeds a product of a multiplier multiplied by a number of signals received by said first circuit, wherein said multiplier is a predetermined number $\geq 1$.

4. An implantable heart stimulating device as claimed in claim 1 wherein said control circuit, during said predetermined time duration, determines whether a number of signals received by said second circuit is substantially twice a number of signals received by said first circuit.

5. An implantable heart stimulating device as claimed in claim 1 wherein said control circuit employs a time duration, as said predetermined time duration, encompassing a plurality of normal heart cycles of the patient.

6. An implantable heart stimulating device as claimed in claim 1 wherein said control circuit performs said detection during a detection time, and wherein said control circuit determines an amplitude of the signal received by said second circuit at least during said detection time, and wherein said control circuit additionally employs a difference in said amplitude for determining whether said signal received by said second circuit is likely to be a far field signal.

7. An implantable heart stimulating device as claimed in claim 6 wherein said control circuit categorizes said signals received by said second circuit into a first category having an amplitude in a first amplitude range and a second category of signals having an amplitude in a second amplitude range, said second amplitude range being lower than said first amplitude range, and wherein said control circuit determines a number of signals in each of said categories and additionally employs said number of signals in each of said categories for determining whether said signal received by said second circuit is likely to be a far field signal.

8. An implantable heart stimulating device as claimed in claim 1 wherein said control circuit performs said detection in a detection time, and wherein said control circuit determines whether a shape of the signals received by said second circuit, at least during said detection time, falls into a first category representing a first type of shape and a second category representing a second type of shape, and wherein said control circuit determines the number of signals in each of said first and second categories and additionally employs said number of signals in each of said first and second categories for determining whether said signal received by said second circuit is likely to be a far field signal.

9. An implantable heart stimulating device as claimed in claim 1 wherein said control circuit performs said detection during a detection time in said predetermined time duration, and wherein said control circuit, at least during said detection time, determines a time spacing between consecutive signals received by said second circuit and additionally employs said time spacing for determining whether said signal received by said second circuit is likely to be a far field signal.

10. An implantable heart stimulating device as claimed in claim 9 wherein said control circuit determines whether said time spacing is less than a predetermined time spacing, and wherein said control circuit additionally employs whether said time spacing is less than said predetermined time spacing for determining whether said signal received by said second circuit is likely to be a far field signal.

11. An implantable heart stimulating device as claimed in claim 10 wherein said control circuit employs a time of less than 500 ms as said predetermined spacing time.

12. An implantable heart stimulating device as claimed in claim 10 wherein said control circuit makes a further determination as to whether consecutive signals having a time spacing therebetween that is less than said predetermined time spacing occur a predetermined number of times or with a predetermined frequency during at least one period during said detection time, and wherein said control circuit additionally employs said further determination for determining whether said signal received by said second circuit is likely to be a far field signal.

13. An implantable heart stimulating device as claimed in claim 1 comprising a third circuit adapted to interact with an atrium of the heart for receiving signals from the atrium, and wherein said control circuit determines whether a first time interval T1 between reception of a signal by said third circuit and a subsequent reception of a signal by said second circuit, and determines whether T1<TA, where TA is a preset time, and wherein said control circuit additionally employs whether an occurrence of T1<TA has occurred for determining whether the signal received by said second circuit is likely to be a far field signal.

14. An implantable heart stimulating device as claimed in claim 13 wherein said control circuit employs a time for TA such that 50 ms $\leq$ TA $\leq$ 150 ms.

15. An implantable heart stimulating device as claimed in claim 1 comprising a third circuit adapted for interacting with an atrium of the heart for delivering pacing pulses to the atrium, and wherein said control circuit determines whether a time interval T1 between delivery of a pacing pulse by said third circuit and a subsequent reception of a signal by the second circuit, and determines whether T1<TA, where TA is a preset time, and wherein said control circuit additionally employs whether an occurrence of T1<TA has occurred for determining whether the signal received by said second circuit is likely to be a far field signal.

16. An implantable heart stimulating device as claimed in claim 15 wherein said control circuit employs a time for TA such that 50 ms$\leq$TA$\leq$150 ms.

17. An implantable heart stimulating device as claimed in claim 1 wherein said control circuit executes a reaction when at least a predetermined number of signals that are likely to be far field signals are detected.

18. An implantable heart stimulating device as claimed in claim 17 comprising a memory, and wherein said control circuit, as said reaction, stores an indication in said memory that a far field signal has been detected.

19. An implantable heart stimulating device as claimed in claim 17 wherein said second circuit has a sensing threshold, and wherein said control circuit, as said reaction, increases said sensing threshold.

20. An implantable heart stimulating device as claimed in claim 17 wherein said control circuit controls delivery of pacing pulses from the first and second circuits dependent on the signals respectively received by said first and second circuits, and wherein said control device, as said reaction, suppresses inclusion of said signals received by said second circuit for controlling delivery of said pacing pulses.

21. An implantable heart stimulating device as claimed in claim 17 wherein said control circuit controls delivery of said pacing pulses from said first and second circuits dependent on the signals respectively received by said first and second circuits, and wherein said control circuit analyzes a shape of the signals received by said second circuit, and wherein said control circuit, as said reaction, suppresses signals received by said second circuit, having a shape comparable to a shape of far field signals, from influencing controlling of the delivery of said pacing pulses.

22. An implantable heart stimulating device as claimed in claim 21 wherein said control circuit operates according to a time cycle corresponding to a normal heart cycle of the patient, and wherein said control circuit, as said reaction, sets a blanking period covering at least a portion of said time cycle corresponding to an occurrence in the time cycle of said signal having a shape comparable to the shape of far field signals, and wherein said control circuit suppresses signals received by said second circuit during said blanking period from the influencing controlling delivery of the pacing pulses.

23. An implantable heart stimulating system comprising:
a first electrode member implantable for interacting with a first ventricle of a heart;
a first sensing and pacing circuit electrically connected to said first electrode member for delivering pacing pulses to and receiving signals from the first ventricle via said first electrode member;
a second electrode member implantable for interaction with a second ventricle of the heart;
a second sensing and pacing circuit electrically connected to said second electrode member for delivering pacing pulses to and receiving signals from the second ventricle via said second electrode member; and
a control circuit connected to said first and second circuits for detecting whether a signal received by said second circuit is likely to be a far field signal, by determining whether, during a predetermined time duration corresponding to at least one normal heart cycle of the patient, more signals are received by said second circuit than by said first circuit.

24. An implantable heart stimulating system as claimed in claim 23 comprising:
a first implantable lead electrically connecting said first sensing and pacing circuit to said first electrode member; and
a second implantable lead electrically connecting said second sensing and pacing circuit to said second electrode member.

25. A method for stimulating a heart comprising the steps of:
implanting a first electrode member in a first ventricle of a heart;
connecting said first electrode member to a first sensing and pacing circuit, and delivering pacing pulses to the first ventricle, from said first sensing and pacing circuit via said first electrode member, and receiving signals from the first ventricle via said first electrode member with said first sensing and pacing circuit;
implanting a second electrode member in a second ventricle of the heart;
electrically connecting a second sensing and pacing circuit to said second electrode member, and delivering pacing pulses from the second sensing and pacing circuit to the second ventricle via said second electrode member, and receiving signals from the second ventricle via said second electrode member with said second sensing and pacing circuit; and
detecting whether a signal received by said second sensing and pacing circuit is likely to be a far field signal by determining whether, during a predetermined time duration corresponding to at least one normal heart cycle of the patient, more signals are received by said second circuit than by said first circuit.

26. A method as claimed in claim 25 comprising implanting said first electrode member in the right ventricle of the heart and implanting said second electrode member in the left ventricle of the heart.

27. A method as claimed in claim 25 comprising implanting a third electrode member in an atrium of the heart;
   electrically connecting a third circuit to said third electrode member and receiving signals from the atrium via said third electrode member with said third circuit; and
   using said signals received from the atrium with said third circuit for additionally assisting in detecting whether said signal received by said second circuit is likely to be a far field signal.

28. A method as claimed in claim 27 comprising implanting said third electrode member in the right atrium of the heart.

29. A method as claimed in claim 25 comprising implanting a third electrode member in an atrium of the heart;
   electrically connecting a third circuit to said third electrode member and delivering pacing pulses from the third circuit to the atrium via said third electrode member; and
   using delivery of said pacing pulses from said third circuit for additionally assisting in detecting whether said signal received by said second circuit is likely to be a far field signal.

30. A method as claimed in claim 29 comprising implanting said third electrode member in the right atrium of the heart.

31. A method as claimed in claim 25 comprising implanting first and second electrode members in the heart of a subject suffering from congestive heart failure, and controlling operation of said first and second sensing and pacing circuits for treating said congestive heart failure.

32. A method as claimed in claim 25 comprising implanting said first and second electrode members in the heart of a patient suffering from bundle branch block, selected from the group consisting of left bundle branch block and right bundle branch block, and controlling said first and second sensing and pacing circuits for treating said bundle branch block.

33. A method as claimed in claim 25 comprising implanting said first and second electrode members in the heart of a patient having an ablated AV-node, and controlling said first and second sensing and pacing circuits according to a pacing and sensing regimen designed for a heart with an ablated AV-node.

34. A method as claimed in claim 25 comprising detecting whether, during said predetermined time duration, more signals are sensed by said second circuit than by said first circuit as an indication of a far field P-wave received by said second circuit.

35. A method as claimed in claim 25 comprising storing information indicating identification of a signal likely to be a far field signal in a memory, and externally accessing said memory for retrieving said information.

* * * * *